US011850250B2

United States Patent
Wu et al.

(10) Patent No.: US 11,850,250 B2
(45) Date of Patent: Dec. 26, 2023

(54) USE OF HOMOHARRINGTONINE IN PREPARATION OF BETACORONAVIRUS REPLICATION INHIBITOR IN HUMAN

(71) Applicant: SUN YAT-SEN UNIVERSITY, Guangzhou (CN)

(72) Inventors: Chungl Wu, Guangzhou (CN); Haijun Wen, Guangzhou (CN)

(73) Assignee: HANGZHOU MINSHENG PHARMACEUTICAL CO., LTD., Hangzhou (CN)

( * ) Notice: Subject to any disclaimer, the term of this patent is extended or adjusted under 35 U.S.C. 154(b) by 48 days.

(21) Appl. No.: 17/407,689

(22) Filed: Aug. 20, 2021

(65) Prior Publication Data

US 2022/0016129 A1    Jan. 20, 2022

Related U.S. Application Data

(63) Continuation-in-part of application No. PCT/CN2020/130845, filed on Nov. 23, 2020.

(30) Foreign Application Priority Data

Mar. 30, 2020  (CN) .......................... 202010233854.X
Sep. 24, 2020  (CN) .......................... 202011018882.6

(51) Int. Cl.
A61K 31/55   (2006.01)
A61P 31/14   (2006.01)

(52) U.S. Cl.
CPC .............. *A61K 31/55* (2013.01); *A61P 31/14* (2018.01)

(58) Field of Classification Search
CPC .................................................... A61K 31/55
See application file for complete search history.

(56) References Cited

FOREIGN PATENT DOCUMENTS

| | | |
|---|---|---|
| CN | 109419804 A | 3/2019 |
| CN | 109745328 A | 5/2019 |
| WO | WO-2021195236 A1 * | 9/2021 |

OTHER PUBLICATIONS

Liang et al. "Development of Small-Molecule MERS-CoV Inhibitors," Viruses, 2018, 10, 721.*
Dyall et al. ("Repurposing of Clinically Developed Drugs for Treatment of Middle East Respiratory Syndrome Coronavirus Infection," Antimicrobial Agents and Chemotherapy, 2014, vol. 58, No. 8, 4885-4893) (Year: 2014).*
Gorbalenya et al. ("The species Severe acute respiratory syndrome-related coronavirus: classifying 2019-nCoV and naming it SARS-CoV-2," Nature Microbiology, 2020, vol. 5, 536-544) (Year: 2020).*
Mustafa Sabeena et al. Current treatment options and the role of peptides as potential therapeutic components for Middle EAST Respiratory Syndrome (MERS): A review, Journal of Infection and Public Health, Feb. 28, 2018, No. 1, vol. 11, pp. 10-11.
Cao Jian Zhong et al. A screen of the NIH Clinical Collection small molecule library identifies potential anti-coronavirus drugs, Antiviral Research, Nov. 18, 2014 (Nov. 18, 2014), vol. 114, pp. 1-10.
Choy Ka-Tim et al. Remdesivir, Iopinavir, emetine, and homoharringtonine inhibit SARS-Cov-2 replication in vitro, Antiviral Research, Apr. 3, 2020, vol. 178, pp. 1-5.
Yang Cheng Wei et al. Repurposing old drugs as antiviral agents for coronaviruses, Biomedical Journal, May 23, 2020 No. 4, vol. 43, p. 370, Table1.
Alvandi et al. U.S. Food and Drug Administration Approval Summary: Omacetaxine Mepesuccinate as Treatment for Chronic Myeloid Leukemia; Office of Clinical Pharmacology, Center for Drug Evaluation and Research, U.S. Food and Drug Administration, Silver Spring, Maryland, USA; The Oncologist 2014;19:94-99; www.TheOncologist.com.
Andersen, Petter I. et al. "Novel Antiviral Activities of Obatoclax, Emetine, Niclosamide, Brequinar, and Homoharringtonine" Viruses 2019, 11, 964; doi: 10.3390/v11100964 www.mdpi.com/journal/viruses.
Cui, Jie et al; "Origin and evolution of pathogenic coronaviruses" Nature Reviews; Microbiology Reviews vol. 17; Mar. 2019.
Dong, Hui-Jun et al. "The Natural Compound Homoharringtonine Presents Broad Antiviral Activity In Vitro and In Vivo" Viruses 2018, 10, 601; doi:10.3390/v10110601 www.mdpi.com/journal/viruses; Nov. 1, 2018.
Hershey, John W.B. et al. "Principles of Translational Control" Cold Spring Harb Perspect Biol 2019;11:a032607.
Jin, Jie et al. "Homoharringtonine-based induction regimens for patients with de-novo acute myeloid leukaemia: a multicentre, open-label, randomised, controlled phase 3 trial" www.thelancet.com/oncology vol. 14 Jun. 2013.
Kaur,Parveen et al. "Inhibition of Chikungunya Virus Replication by Harringtonine, a Novel Antiviral That Suppresses Viral Protein Expression" Jan. 2013 vol. 57 No. 1 Antimicrobial Agents and Chemotherapy p. 155-167 aac.asm.org.

(Continued)

*Primary Examiner* — Yong S. Chong
(74) *Attorney, Agent, or Firm* — D'Ambrosio & Menon, PLLC; Usha Menon (57) ABSTRACT

Disclosed is a use of homoharringtonine (HHT) in preparation of a drug against betacoronavirus infection, a use of homoharringtonine in preparation of a betacoronavirus replication inhibitor in human, and a formulation and a method for treating a disease caused by betacoronavirus. Through research, the HHT is found to not only have a good inhibitory effect on the first step of protein synthesis, but also have an unexpected inhibitory effect on each step of protein synthesis elongation, and can better inhibit the synthesis of long proteins. Because betacoronaviruses have longer ORFs and are more sensitive to the HHT, the HHT has a better replication inhibition effect on the betacoronaviruses, thus providing a feasible solution for controlling the replication of coronaviruses. The effects of the HHT on treating diseases caused by the betacoronaviruses including SARS-CoV-2 are confirmed for the first time by cell experiments and animal models.

7 Claims, 9 Drawing Sheets

(56) References Cited

OTHER PUBLICATIONS

Lam, Stephen S. Y. et al; "Homoharringtonine (omacetaxine mepesuccinate) as an adjunct for FLT3-ITD acute myeloid leukemia;" Sci. Transl. Med. 8, 359ra129; Oct. 5, 2016.
Sanchez-Petitto et al. "Omacetaxine mepesuccinate for patients with higher risk MDS and CMML after failure of hypomethylating agents: A phase II Clinical Trial" 2018; American Society of Clinical Oncology.
Tahmasebi,Soroush et al. "Protein Synthesis and Translational Control: A Historical Perspective;" Cold Spring Harb Perspect Biol 2019;11:a035584.
Shen Liang et al; "High-throughput screening and identification of potent broad spectrum inhibitors of coronaviruses;" Jun. 2019 vol. 93 Issue 12 e00023-19; Journal of Virology; jvi.asm.org.
Dyall, Julie et al.; "Repurposing of Clinically Developed Drugs for Treatment of Middle East Respiratory Syndrome Coronavirus Infection" Aug. 2014 vol. 58 No. 8; Antimicrobial Agents and Chemotherapy p. 4885-4893; aac.asrn.org.

* cited by examiner

USE OF HOMOHARRINGTONINE IN PREPARATION OF BETACORONAVIRUS REPLICATION INHIBITOR IN HUMAN

CROSS-REFERENCE TO RELATED APPLICATION

The present disclosure is based on and claims the priority of the Chinese Patent Application No. 202011018882.6, filed on Sep. 24, 2020, and the Chinese Patent Application No. 202010233854.X, filed on Mar. 30, 2020, the entire contents of which are incorporated herein by reference.

TECHNICAL FIELD

The embodiments of the present disclosure relate to a new use of a compound, and more particularly, to a use of homoharringtonine in preparation of a drug against betacoronavirus infection, a use of homoharringtonine in preparation of a betacoronavirus replication inhibitor in human, and a formulation and method for treating a disease caused by betacoronavirus.

BACKGROUND

Homoharringtonine (HHT) is an alkaloid extracted from *Cephalotaxus fortunei* or a congener thereof. The homoharringtonine is a frequently-used protein synthesis inhibitor and has been approved for the treatment of various leukemia and lymphoma (Jin, et al. 2013; Alvandi, et al. 2014; Lam, et al. 2016; Sanchez-Petitto, et al. 2018). Several studies in cell models or animal models have shown that the homoharringtonine has a certain effect on inhibiting virus replication (Kaur, et al. 2013; Cao, et al. 2015; Dong, et al. 2018; Andersen, et al. 2019). A recommended dose of the homoharringtonine for treating tumors is: intravenous drip: 1 mg to 4 mg/day, and 4 days to 6 days as a course of treatment.

The existing studies believe that the HHT achieves the effect of inhibiting virus replication by inhibiting the first step of protein synthesis.

CN109419804A discloses that the homoharringtonine (HHT) has broad-spectrum and high-efficiency antiviral activity, which can effectively inhibit 9 viruses (VSV, NDV, PEDV, TGEV, AIV, HSV-1, PRV, PRRSV, FMDV) belonging to 7 families from infecting host cells and animals (chickens, chicken embryos, pigs, or the like), significantly reduce the amounts of viruses in animals, and relieve infection symptoms. Specifically, when the HHT is used at a concentration of 20 nM to 300 nM, it can effectively inhibit 9 viruses (VSV, NDV, PEDV, TGEV, AIV, HSV-1, PRV, PRRSV, and FMDV) belonging to 7 families from infecting the host cells (HeLa, Vero, Marc145, PK15 cells, or the like). The influence result of the HHT on FMDV virus virulence (see FIG. 9 of CN109419804A) shows that in PK-15 cells, the HHT at a concentration of 50 nM can almost completely block the expression of FMDV virus proteins VP0, VP1, VP2 and VP3.

CN109745328A discloses a use of the homoharringtonine in preparation of a drug for preventing foot-and-mouth disease virus (FMDV) infection. The experimental data verifies that the homoharringtonine can provide effective protection for IBRS-2 cells only when the concentration of the HHT is 6.2 μM or higher. At the same time, the experimental data shows that the HHT will not affect the adsorption of FMDV and will not affect the ability of the virus to enter cells. The HHT only plays a role in the early stage of FMDV replication, but cannot prevent virus replication in the later stage of virus replication.

The experimental data disclosed by CN109745328A and CN109419804A suggest that, for the foot-and-mouth disease virus (FMDV) infection, the HHT plays different roles in different cells (IBRS-2 cells are used in CN109745328A, and PK-15 cells are used in CN109419804A), and differences of the effective concentrations of the HHT are more than 100 times (the concentration required in CN109745328A is more than 6.2 μM, while the concentration required in CN109419804A is 50 nM).

Therefore, it is necessary to deeply study the mechanisms of action of HHT, identify the indications of HHT in antiviral therapy, and develop new ways of administration so that the HHT can really be used in antiviral clinical therapy.

Coronaviruses are one of the main viral pathogens causing respiratory tract infections. According to genetic and antigenic criteria, the coronaviruses may be divided into four genera, namely alphacoronavirus, betacoronavirus, gammacoronavirus and deltacoronavirus. Up to now, seven coronaviruses (HCoV-229E, HCoV-OC43, SARS-CoV, HCoV-NL63, HCoV-HKU1, MERS-CoV, and SARS-CoV-2 which recently caused COVID-19) have been found to infect humans. HCoV-229E and HCoV-NL63 belong to alphacoronaviruses, while HCoV-OC43, SARS-CoV, HCoV-HKU1, MERS-CoV and SARS-CoV-2 are all betacoronaviruses. Beside humans, the coronaviruses can also cause multisystem infection in a plurality of animals. Mammalian coronaviruses are mainly alphacoronaviruses and betacoronaviruses, which can infect a plurality of animals including pigs, dogs, cats, mice, cattle, horses, and the like. Avian coronaviruses mainly come from gammacoronaviruses and deltacoronaviruses, which can cause diseases of a plurality of birds such as chickens, turkeys, sparrows, ducks, geese and pigeons (Cui, et al. 2019). Common coronaviruses are shown in Table 1.

TABLE 1

| Common coronaviruses | |
|---|---|
| Classification | Coronavirus |
| Alphacoronavirus | Pig epidemic diarrhea virus (PEDV), human coronavirus NL63(HCoV-NL63), human coronavirus 229E (HCoV-229E), canine coronavirus (CCoV) and transmissible gastroenteritis virus (TGEV) |
| Betacoronavirus | HCoV-OC43, SARS-CoV, MERS-CoV, SARS-CoV-2, and HCoV-HKU1 |
| Gammacoronavirus | Avian infectious bronchitis virus (IBV) |
| Deltacoronavirus | Parrot coronavirus (PaCoV), and porcine deltacoronavirus (PdCoV) |

There are obvious differences among different coronaviruses. For example, both belonging to the betacoronaviruses, the similarity of full-length genome sequences between SARS-CoV and SARS-CoV-2 is only about 80%, and the sequence similarity of S gene (encoding a spike protein responsible for receptor binding, which is closely related to virus pathogenicity) is only 73%, thus leading to difference of biological characteristics of pathogens between SARS-CoV and SARS-CoV-2, including severe illness rate, mortality rate, transmission ability, latency, and the like. The differences among coronaviruses belonging to different genus's are more obvious. For example, the betacoronaviruses such as HCoV-OC43, SARS-CoV, MERS-CoV and SARS-CoV-2 have longer open reading frames (ORFs) than those of the alphacoronaviruses. In addition, there are obvious differences between the alphacoronaviruses and the betacoronaviruses in hosts, pathogenicity, host cell receptors, vaccines and potential therapeutic drugs.

In recent years, the coronaviruses have done great harm to human beings. From 2002 to 2003, SARS-CoV caused an unprecedented "SARS" epidemic in the world, resulting in more than 8000 cases of infection and more than 800 cases of death. In 2012, MERS-CoV was first discovered in the The embodiment according to a second aspect of the present invention provides: use of homoharringtonine in preparation of a betacoronavirus replication inhibitor in a human.

In some embodiments, the betacoronavirus is selected from HCoV-HKU1, HCoV-OC43, SARS-CoV, MERS-CoV and SARS-CoV-2.

In some embodiments, the betacoronavirus is SARS-CoV-2.

In some embodiments, the inhibitor is in a dosage form of injection, oral formulation or inhalant.

The embodiment according to a third aspect of the present invention provides: a formulation for treating a disease caused by betacoronavirus, comprising at least one drug capable of improving the symptoms caused by betacoronavirus infection, and homoharringtonine, wherein the homoharringtonine is used for inhibiting replication of the betacoronavirus in vivo.

In some embodiments, the betacoronavirus is selected from HCoV-HKU1, HCoV-OC43, SARS-CoV, MERS-CoV and SARS-CoV-2.

In some embodiments, the betacoronavirus is SARS-CoV-2.

In some embodiments, the formulation is in a dosage form of injection, oral formulation or inhalant.

In some embodiments, the formulation further comprises an acceptable pharmaceutical excipient.

The embodiment according to a fourth aspect of the present invention provides: a method for treating a disease caused by betacoronavirus, comprises the administration of homoharringtonine to patients.

In some embodiments, the betacoronavirus is selected from HCoV-HKU1, HCoV-OC43, SARS-CoV, MERS-CoV and SARS-CoV-2.

In some embodiments, the betacoronavirus is SARS-CoV-2.

In some embodiments, the method further comprises administering at least one drug capable of improving the symptoms caused by betacoronavirus infection in patients.

(1) Inhibiting the elongation step in protein synthesis is an effective method to control the protein synthesis.

The protein synthesis comprises the steps of initiation, elongation, termination, and recycling (Hershey, et al. 2019; Tahmasebi, et al. 2019). By controlling the elongation step in the protein synthesis, the protein synthesis can be effectively controlled, especially for those long proteins. The specific theoretical basis is:

$$T(p) = (1-p)^k \sim e^{-pk} \quad \text{(Formula 1)}.$$

In the formula, p is the inhibitory effect on each step, k is the number of elongation steps of the protein (which may be understood as a length of a polypeptide chain), and T(p) is a cumulative effect on the full-length protein.

According to this formula, when the inhibitory effect on a protein with a length of 500 amino acids is 20%, the inhibitory effect on a protein with a length of 8000 amino acids is 96%.

Therefore, inhibiting the elongation step in protein synthesis is the effective method to control the protein synthesis, and especially for long protein synthesis.

(2) The first step of coronaviruses replication needs to encode a very long protein (ORF1ab, nearly 800 Kda), which may be particularly sensitive to a protein elongation inhibitor, thus providing a feasible solution for controlling coronaviruses replication.

Figure 1:
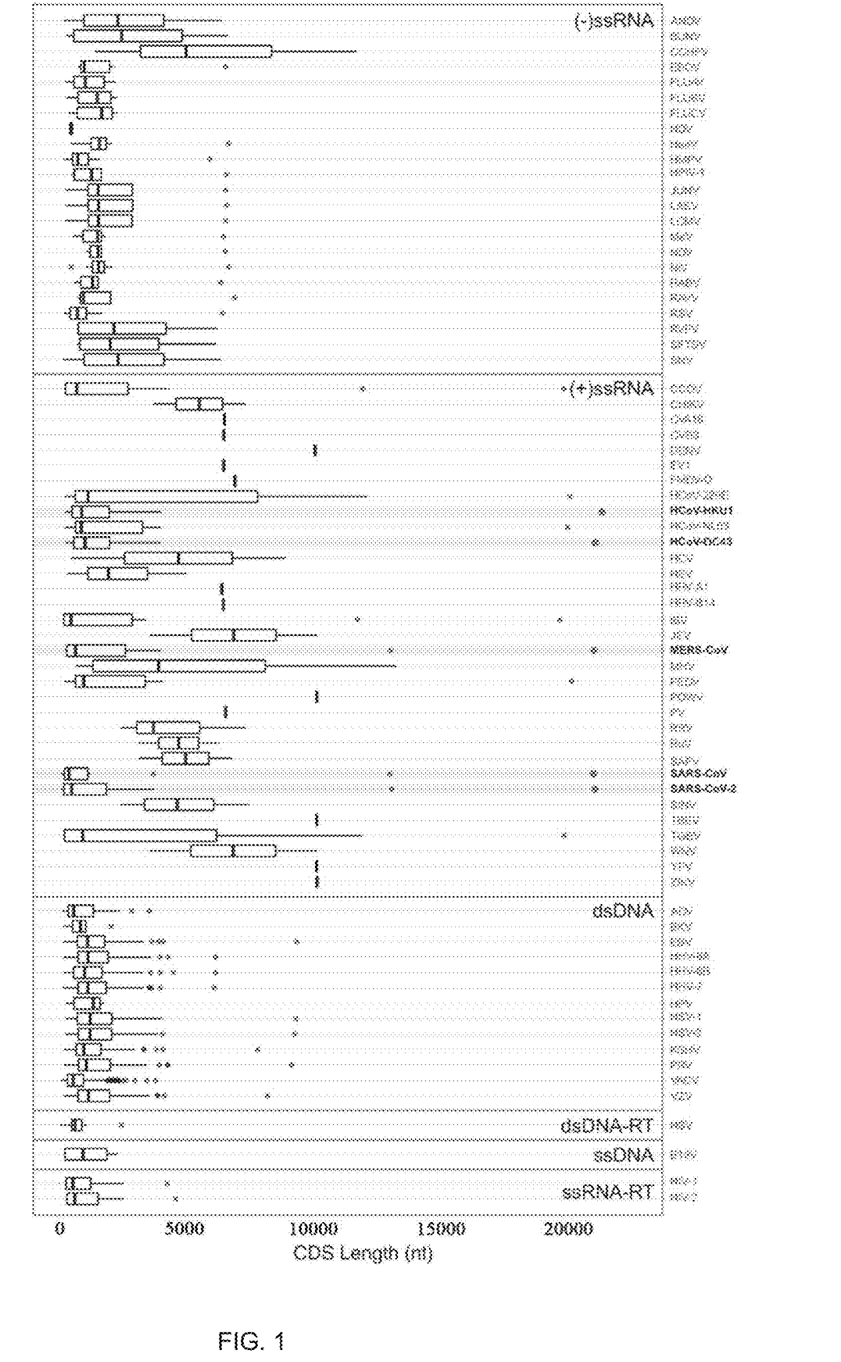
Figure 2:
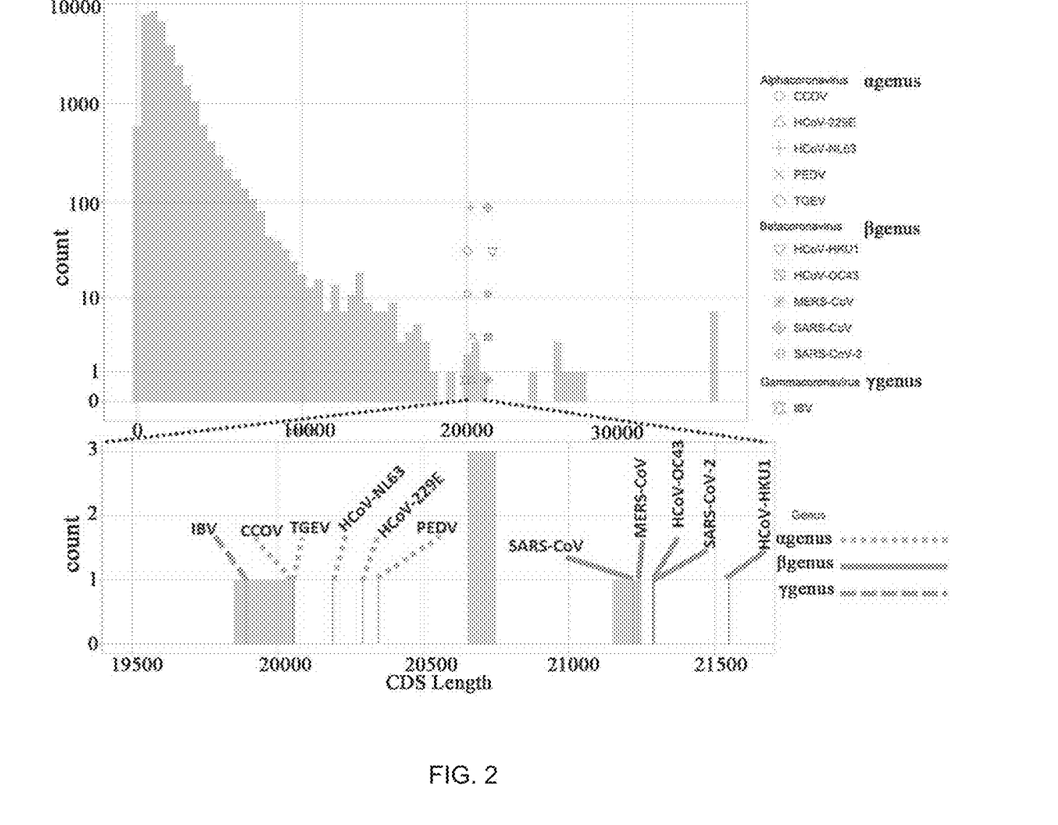

By analyzing sequence information of viral genomes related to human diseases, the inventors found that several Coronaviridae viruses, such as HCoV-HKU1, HCoV-OC43, MERS-CoV, SARS-CoV, and SARS-CoV-2, had particularly long open reading frames (ORFs) with the length of over 20,000 nucleotides (FIG. 1). It was particularly noteworthy that the ORFs of the betacoronaviruses were generally longer than those of alphacoronaviruses, and far exceeded most genes in a human genome (FIG. 2).

Therefore, the key genes in the process of virus replication can be inhibited by inhibiting the elongation step of the protein synthesis, while the protein synthesis of most genes in the human genome is not affected too much.

(3) Long proteins in mammalian genomes have a long half-life, so the long proteins are less affected by a protein synthesis inhibitor.

Figure 3A:
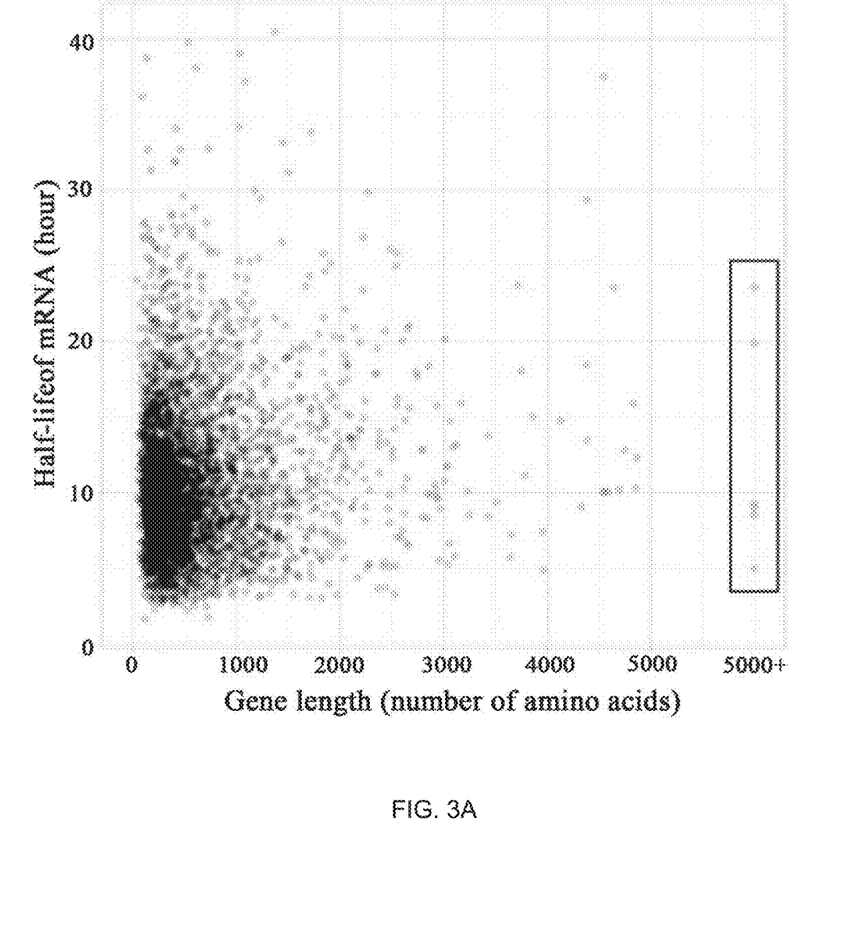
Figure 3B:
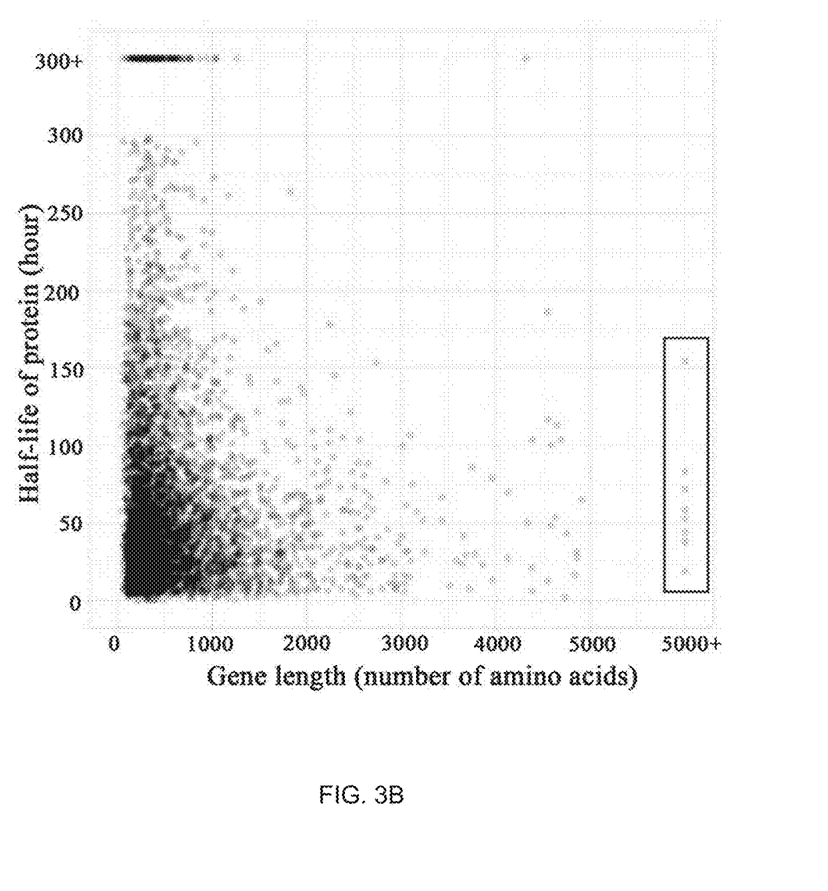

Since inhibiting the elongation step of the protein synthesis has less influence on short proteins and more obvious influence on long proteins in theory, it is necessary to pay special attention to the half-lives of those long proteins in the human genome, so as to evaluate the influence of this treatment method. By analyzing the half-lives of mRNAs and proteins of a large number of genes in the genome, the inventors found for the first time that the median half-lives of the mRNAs and the proteins of the genes encoding long proteins (over 5000 amino acids in length) were 8.3 hours and 56 hours respectively. The results showed that the median half-life of the long protein was longer than that of all the genes in the genome (FIG. 3A and FIG. 3B). The results indicate that inhibiting the elongation step of the protein synthesis in a short time will not significantly reduce the expression level of the long protein, and will not cause great damage to the patient.

(4) Study on the toxicity of homoharringtonine to human cells.

Figure 4:
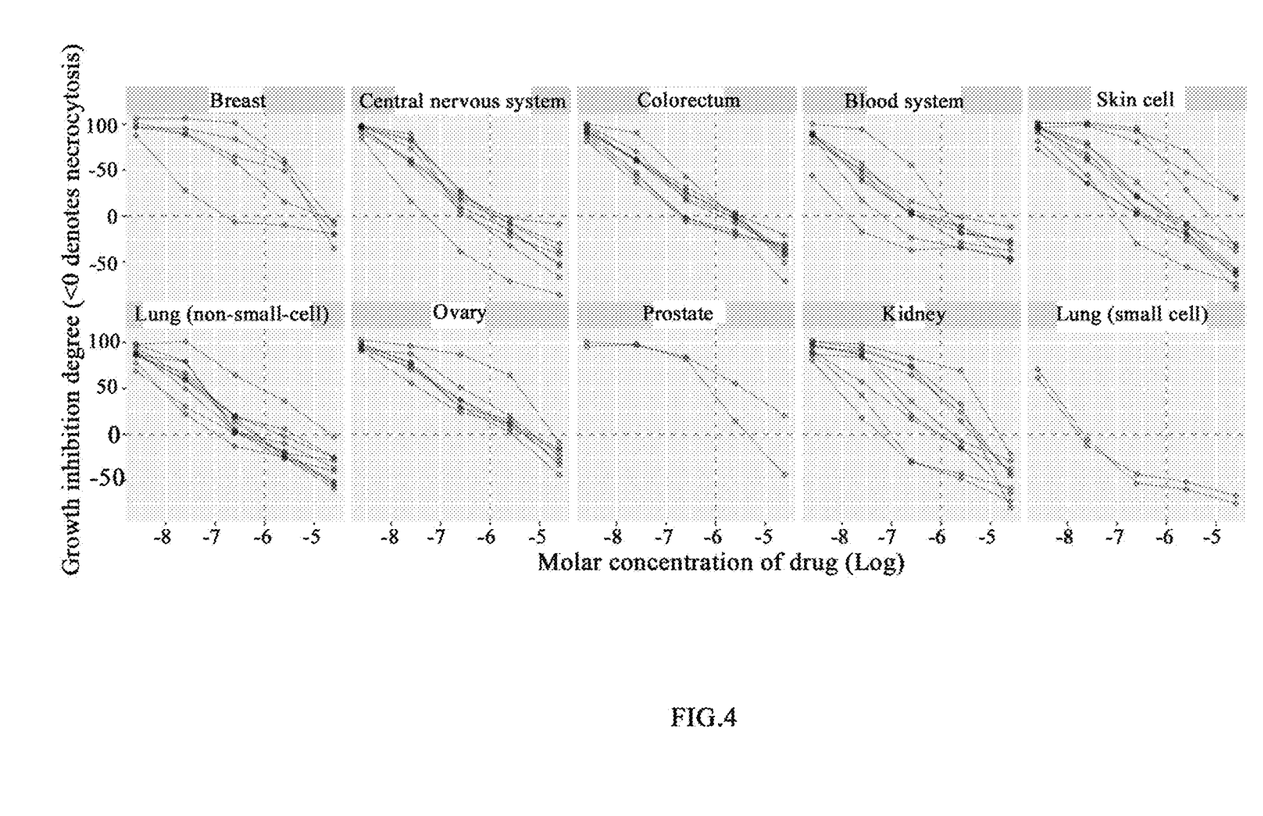

By analyzing the effect of Homoharringtonine on 60 human cell lines, the inventors found that only a few cells died obviously after being treated with 1 micromolar ($\mu$M) concentration (or lower concentration) for 48 hours, and the cell viability in other cell lines was about 100% (FIG. 4). However, with the increase of the drug concentration, the toxicity of the HHT to the cells was more obvious. The inventors speculate that the HHT is relatively safe to human when its concentration is lower than 1 micromole ($\mu$M), but if its concentration is further increased, it will cause obvious damage.

(5) Expression of long proteins in human genome.

The expression of those particularly long proteins (more than 5,000 amino acids in length) in human organs and tissues was analyzed, and the details were shown in Table 2.

TABLE 2

Expression of long proteins in genomes in 29 organs and tissues of healthy human

| Name of gene | CDS length | Suprarenal gland | Appendix | Brain | Colon | Duodenum |
|---|---|---|---|---|---|---|
| TTN | 107976 | 5.3E+06 | 7.3E+06 | 8.1E+06 | 8.1E+06 | 6.5E+06 |
| MUC16 | 43524 | 1.2E+04 | 1.1E+05 | 8.4E+04 | 3.7E+04 | 2.2E+04 |

TABLE 2-continued

Expression of long proteins in genomes in 29 organs and tissues of healthy human

| Name of gene | CDS length | | | | |
|---|---|---|---|---|---|
| OBSCN | 26772 | 1.4E+06 | 9.6E+05 | 3.0E+05 | 2.4E+06 | 1.2E+06 |
| SYNE1 | 26394 | 1.3E+07 | 5.8E+06 | 3.5E+07 | 8.8E+06 | 8.8E+06 |
| NEB | 25683 | 4.7E+05 | 3.6E+05 | 1.9E+06 | 5.6E+05 | 8.8E+04 |
| SYNE2 | 20724 | 6.2E+06 | 7.4E+06 | 3.6E+06 | 1.8E+07 | 1.3E+07 |
| MACF1 | 17817 | 2.3E+07 | 3.1E+07 | 3.4E+07 | 1.3E+07 | 1.5E+07 |
| AHNAK | 17673 | 4.8E+08 | 6.1E+08 | 1.4E+08 | 1.1E+09 | 7.9E+08 |
| AHNAK2 | 17388 | 1.0E+06 | 9.0E+06 | 1.3E+07 | 1.4E+07 | 2.2E+07 |
| MUC5B | 17289 | 1.3E+06 | 2.8E+05 | 1.8E+05 | 7.1E+05 | 2.4E+05 |
| DST | 17028 | 1.3E+07 | 8.1E+06 | 4.4E+07 | 1.8E+07 | 8.0E+07 |
| MUC5AC | 16965 | 1.2E+06 | 3.3E+06 | 2.7E+06 | 1.1E+07 | 2.1E+07 |
| HMCN1 | 16908 | 2.3E+05 | 4.9E+06 | 5.6E+05 | 1.7E+06 | 3.4E+06 |
| MDN1 | 16791 | 1.5E+06 | 1.1E+06 | 7.8E+05 | 9.2E+05 | 2.1E+06 |
| KMT2D | 16614 | 7.6E+04 | 4.9E+05 | 2.8E+05 | 8.0E+05 | 4.6E+05 |
| MUC4 | 16239 | 1.2E+05 | 2.9E+05 | 0.0E+00 | 4.0E+06 | 3.1E+05 |
| MUC12 | 16008 | 0.0E+00 | 3.5E+05 | 2.2E+05 | 2.6E+06 | 1.6E+05 |
| RNF213 | 15771 | 1.3E+07 | 2.4E+07 | 3.8E+06 | 1.1E+07 | 1.6E+07 |
| UBR4 | 15552 | 2.5E+07 | 1.2E+07 | 2.2E+07 | 1.6E+07 | 1.9E+07 |
| PCLO | 15429 | 3.2E+06 | 1.1E+06 | 1.0E+07 | 3.8E+06 | 6.3E+05 |
| HYDIN | 15366 | 7.4E+05 | 7.8E+05 | 2.7E+05 | 1.3E+05 | 8.5E+04 |
| EPPK1 | 15267 | 3.3E+05 | 4.0E+06 | 1.0E+06 | 3.5E+07 | 6.8E+07 |
| KIAA1109 | 15018 | 1.6E+06 | 6.0E+04 | 1.3E+06 | 2.2E+06 | 1.3E+06 |

| Name of gene | CDS length | Endometrium | Esophagus | Salpinx | Fat | Gallbladder |
|---|---|---|---|---|---|---|
| TTN | 107976 | 6.1E+06 | 6.4E+06 | 3.3E+06 | 2.1E+07 | 2.0E+07 |
| MUC16 | 43524 | 6.8E+04 | 2.8E+04 | 1.6E+04 | 4.6E+04 | 0.0E+00 |
| OBSCN | 26772 | 1.4E+06 | 7.4E+05 | 1.2E+06 | 1.9E+06 | 2.2E+06 |
| SYNE1 | 26394 | 1.2E+07 | 8.6E+06 | 3.6E+07 | 6.8E+06 | 8.2E+06 |
| NEB | 25683 | 3.3E+04 | 3.5E+05 | 3.6E+05 | 5.8E+04 | 2.9E+04 |
| SYNE2 | 20724 | 1.9E+07 | 6.2E+06 | 2.7E+07 | 1.2E+07 | 1.0E+07 |
| MACF1 | 17817 | 7.2E+07 | 4.7E+07 | 2.5E+07 | 1.6E+07 | 4.6E+07 |
| AHNAK | 17673 | 1.6E+09 | 1.1E+09 | 1.2E+09 | 1.5E+09 | 1.0E+09 |
| AHNAK2 | 17388 | 6.0E+07 | 1.3E+08 | 1.3E+08 | 1.4E+07 | 2.2E+07 |
| MUC5B | 17289 | 6.0E+05 | 4.6E+05 | 1.1E+05 | 1.0E+06 | 1.7E+08 |
| DST | 17028 | 2.4E+07 | 8.5E+07 | 4.6E+06 | 5.3E+06 | 2.4E+07 |
| MUC5AC | 16965 | 8.8E+05 | 1.8E+06 | 4.8E+05 | 5.8E+06 | 3.7E+07 |
| HMCN1 | 16908 | 1.4E+06 | 5.9E+06 | 1.1E+06 | 8.1E+05 | 8.6E+06 |
| MDN1 | 16791 | 1.2E+06 | 3.2E+05 | 1.9E+06 | 1.1E+06 | 7.2E+05 |
| KMT2D | 16614 | 3.4E+05 | 1.9E+05 | 1.2E+06 | 3.5E+05 | 1.8E+04 |
| MUC4 | 16239 | 3.9E+04 | 0.0E+00 | 2.9E+05 | 0.0E+00 | 0.0E+00 |
| MUC12 | 16008 | 0.0E+00 | 0.0E+00 | 0.0E+00 | 0.0E+00 | 0.0E+00 |
| RNF213 | 15771 | 9.3E+06 | 1.0E+07 | 1.6E+07 | 1.0E+07 | 1.9E+07 |
| UBR4 | 15552 | 2.2E+07 | 1.3E+07 | 1.7E+07 | 1.3E+07 | 1.7E+07 |
| PCLO | 15429 | 6.4E+04 | 4.0E+05 | 3.1E+06 | 2.9E+05 | 5.9E+05 |
| HYDIN | 15366 | 1.1E+06 | 2.4E+06 | 5.6E+06 | 1.1E+06 | 8.1E+04 |
| EPPK1 | 15267 | 8.0E+06 | 5.3E+07 | 5.5E+07 | 1.3E+06 | 1.0E+07 |
| KIAA1109 | 15018 | 2.6E+06 | 6.3E+05 | 2.1E+06 | 2.4E+04 | 2.0E+05 |

| Name of gene | CDS length | Heart | Kidney | Liver | Lung | Lymph node |
|---|---|---|---|---|---|---|
| TTN | 107976 | 3.8E+09 | 3.9E+06 | 2.9E+06 | 1.0E+07 | 2.3E+06 |
| MUC16 | 43524 | 1.2E+04 | 4.0E+04 | 1.8E+05 | 2.5E+05 | 3.4E+04 |
| OBSCN | 26772 | 3.9E+08 | 6.3E+05 | 1.2E+06 | 7.6E+05 | 9.7E+05 |
| SYNE1 | 26394 | 9.9E+06 | 7.2E+06 | 2.2E+07 | 4.7E+06 | 1.0E+07 |
| NEB | 25683 | 6.4E+06 | 1.0E+06 | 7.0E+05 | 1.0E+06 | 2.3E+04 |
| SYNE2 | 20724 | 3.0E+07 | 3.4E+07 | 1.5E+07 | 1.2E+07 | 1.1E+07 |
| MACF1 | 17817 | 4.5E+07 | 3.1E+07 | 2.3E+07 | 2.7E+07 | 1.7E+07 |
| AHNAK | 17673 | 1.1E+09 | 3.2E+08 | 2.2E+08 | 4.0E+08 | 8.3E+08 |
| AHNAK2 | 17388 | 3.7E+06 | 1.3E+06 | 9.1E+05 | 2.8E+06 | 3.7E+06 |
| MUC5B | 17289 | 7.7E+05 | 2.6E+05 | 1.9E+05 | 7.3E+06 | 1.0E+06 |
| DST | 17028 | 2.4E+08 | 6.3E+06 | 1.3E+07 | 2.3E+07 | 2.2E+07 |
| MUC5AC | 16965 | 4.3E+06 | 6.6E+05 | 2.4E+06 | 8.1E+05 | 7.3E+05 |
| HMCN1 | 16908 | 1.2E+06 | 3.7E+05 | 6.0E+05 | 2.7E+06 | 3.6E+05 |
| MDN1 | 16791 | 3.3E+05 | 8.1E+05 | 1.8E+06 | 2.9E+06 | 2.1E+06 |
| KMT2D | 16614 | 3.3E+05 | 2.2E+05 | 1.1E+05 | 9.0E+05 | 1.3E+06 |
| MUC4 | 16239 | 0.0E+00 | 3.1E+04 | 0.0E+00 | 4.8E+05 | 0.0E+00 |
| MUC12 | 16008 | 0.0E+00 | 0.0E+00 | 0.0E+00 | 0.0E+00 | 0.0E+00 |

TABLE 2-continued

Expression of long proteins in genomes in 29 organs and tissues of healthy human

| | | | | | |
|---|---|---|---|---|---|
| RNF213 | 15771 | 2.0E+06 | 5.2E+06 | 1.4E+07 | 5.6E+07 | 2.9E+07 |
| UBR4 | 15552 | 2.1E+07 | 1.8E+07 | 2.3E+07 | 2.6E+07 | 1.5E+07 |
| PCLO | 15429 | 4.3E+05 | 8.3E+05 | 2.9E+06 | 2.9E+06 | 1.4E+05 |
| HYDIN | 15366 | 2.9E+05 | 1.1E+06 | 6.8E+04 | 2.3E+05 | 1.1E+06 |
| EPPK1 | 15267 | 1.5E+06 | 1.0E+07 | 4.2E+06 | 5.8E+06 | 3.3E+06 |
| KIAA1109 | 15018 | 0.0E+00 | 4.5E+05 | 1.5E+05 | 1.2E+05 | 6.0E+05 |

| Name of gene | CDS length | Ovary | Pancreas | Placenta | Prostate | Rectum |
|---|---|---|---|---|---|---|
| TTN | 107976 | 7.0E+06 | 1.7E+07 | 6.8E+06 | 5.8E+06 | 5.4E+06 |
| MUC16 | 43524 | 2.8E+04 | 0.0E+00 | 7.1E+04 | 0.0E+00 | 3.2E+04 |
| OBSCN | 26772 | 1.2E+06 | 4.7E+06 | 6.7E+05 | 7.2E+05 | 8.1E+05 |
| SYNE1 | 26394 | 6.4E+06 | 1.0E+07 | 3.9E+06 | 8.0E+06 | 8.2E+06 |
| NEB | 25683 | 1.6E+05 | 2.5E+06 | 1.6E+05 | 4.8E+06 | 6.8E+04 |
| SYNE2 | 20724 | 2.9E+07 | 1.1E+07 | 3.6E+07 | 9.3E+06 | 1.2E+07 |
| MACF1 | 17817 | 3.3E+07 | 3.9E+07 | 7.1E+07 | 3.2E+07 | 5.6E+07 |
| AHNAK | 17673 | 2.3E+09 | 5.1E+08 | 7.9E+08 | 5.5E+08 | 1.8E+09 |
| AHNAK2 | 17388 | 8.4E+07 | 5.4E+06 | 5.3E+06 | 1.7E+07 | 9.1E+07 |
| MUC5B | 17289 | 9.6E+05 | 6.3E+05 | 4.9E+05 | 2.2E+06 | 5.9E+06 |
| DST | 17028 | 3.7E+07 | 6.7E+06 | 4.8E+06 | 1.3E+07 | 1.1E+07 |
| MUC5AC | 16965 | 1.3E+06 | 1.8E+06 | 1.8E+06 | 1.2E+06 | 1.1E+07 |
| HMCN1 | 16908 | 1.6E+07 | 4.8E+05 | 5.4E+05 | 2.3E+06 | 7.6E+05 |
| MDN1 | 16791 | 1.4E+06 | 3.0E+06 | 6.7E+05 | 1.5E+06 | 9.3E+05 |
| KMT2D | 16614 | 5.9E+05 | 1.7E+05 | 7.9E+05 | 1.2E+05 | 2.4E+05 |
| MUC4 | 16239 | 0.0E+00 | 0.0E+00 | 5.4E+06 | 3.8E+05 | 4.6E+06 |
| MUC12 | 16008 | 0.0E+00 | 0.0E+00 | 0.0E+00 | 0.0E+00 | 4.5E+06 |
| RNF213 | 15771 | 9.3E+06 | 1.0E+07 | 8.7E+06 | 5.5E+06 | 7.9E+06 |
| UBR4 | 15552 | 9.3E+06 | 1.9E+07 | 3.5E+07 | 1.8E+07 | 1.6E+07 |
| PCLO | 15429 | 0.0E+00 | 3.1E+06 | 5.7E+05 | 3.7E+05 | 6.3E+04 |
| HYDIN | 15366 | 1.0E+05 | 2.9E+04 | 2.2E+05 | 3.4E+05 | 7.9E+05 |
| EPPK1 | 15267 | 1.2E+08 | 5.0E+07 | 2.3E+07 | 3.2E+07 | 6.0E+07 |
| KIAA1109 | 15018 | 7.2E+05 | 6.9E+04 | 2.9E+05 | 2.6E+05 | 1.1E+06 |

| Name of gene | CDS length | Salivary gland | Small intestine | Smooth muscle | Spleen | Stomach |
|---|---|---|---|---|---|---|
| TTN | 107976 | 2.5E+06 | 2.8E+07 | 1.0E+07 | 6.7E+06 | 4.4E+06 |
| MUC16 | 43524 | 1.0E+05 | 1.7E+07 | 6.8E+04 | 6.1E+06 | 7.8E+03 |
| OBSCN | 26772 | 1.7E+06 | 8.6E+05 | 4.1E+05 | 4.7E+05 | 4.7E+05 |
| SYNE1 | 26394 | 1.8E+07 | 1.6E+07 | 1.4E+07 | 1.9E+07 | 2.3E+07 |
| NEB | 25683 | 7.4E+03 | 1.1E+05 | 3.0E+04 | 9.7E+03 | 5.7E+05 |
| SYNE2 | 20724 | 7.3E+06 | 1.4E+07 | 1.9E+07 | 1.5E+07 | 2.2E+07 |
| MACF1 | 17817 | 4.4E+07 | 1.7E+07 | 6.8E+07 | 2.4E+07 | 3.5E+07 |
| AHNAK | 17673 | 3.5E+08 | 5.7E+08 | 1.8E+09 | 4.7E+08 | 1.2E+09 |
| AHNAK2 | 17388 | 2.3E+06 | 5.8E+06 | 4.4E+07 | 6.3E+05 | 2.2E+07 |
| MUC5B | 17289 | 2.7E+08 | 3.5E+05 | 1.3E+06 | 1.2E+06 | 7.0E+06 |
| DST | 17028 | 7.2E+07 | 2.1E+07 | 1.2E+08 | 1.1E+07 | 1.3E+07 |
| MUC5AC | 16965 | 2.1E+07 | 1.5E+07 | 2.1E+06 | 6.9E+05 | 3.3E+09 |
| HMCN1 | 16908 | 5.2E+05 | 2.3E+05 | 4.1E+06 | 2.1E+06 | 5.7E+05 |
| MDN1 | 16791 | 4.6E+05 | 1.8E+06 | 7.3E+05 | 3.2E+05 | 6.9E+05 |
| KMT2D | 16614 | 7.1E+05 | 5.7E+05 | 1.5E+05 | 3.8E+05 | 6.3E+05 |
| MUC4 | 16239 | 2.1E+04 | 1.7E+05 | 0.0E+00 | 6.7E+05 | 1.0E+05 |
| MUC12 | 16008 | 3.8E+04 | 0.0E+00 | 2.0E+05 | 0.0E+00 | 0.0E+00 |
| RNF213 | 15771 | 1.4E+07 | 3.4E+07 | 7.1E+06 | 3.3E+07 | 1.2E+07 |
| UBR4 | 15552 | 3.0E+07 | 1.8E+07 | 1.7E+07 | 1.7E+07 | 1.5E+07 |
| PCLO | 15429 | 5.2E+05 | 4.3E+06 | 1.3E+05 | 2.2E+04 | 6.8E+05 |
| HYDIN | 15366 | 2.8E+05 | 7.4E+05 | 3.7E+05 | 1.8E+06 | 8.6E+04 |
| EPPK1 | 15267 | 1.4E+08 | 5.7E+07 | 1.5E+07 | 7.8E+06 | 9.4E+06 |
| KIAA1109 | 15018 | 5.3E+05 | 1.1E+06 | 4.7E+05 | 7.2E+05 | 5.2E+05 |

| Name of gene | CDS length | Testis | Thyroid gland | Tonsil | Bladder |
|---|---|---|---|---|---|
| TTN | 107976 | 3.0E+06 | 1.1E+07 | 1.5E+07 | 1.0E+07 |
| MUC16 | 43524 | 2.6E+04 | 4.2E+04 | 5.4E+04 | 1.3E+04 |
| OBSCN | 26772 | 2.3E+06 | 1.4E+06 | 2.4E+05 | 1.2E+06 |
| SYNE1 | 26394 | 1.5E+07 | 9.8E+06 | 5.3E+06 | 9.7E+06 |
| NEB | 25683 | 1.7E+04 | 5.5E+05 | 3.4E+06 | 2.2E+05 |
| SYNE2 | 20724 | 5.7E+07 | 2.3E+07 | 1.7E+07 | 1.1E+07 |
| MACF1 | 17817 | 3.8E+07 | 3.8E+07 | 1.5E+07 | 1.5E+07 |
| AHNAK | 17673 | 9.8E+08 | 2.1E+08 | 5.4E+08 | 5.8E+08 |
| AHNAK2 | 17388 | 3.9E+05 | 1.4E+06 | 4.1E+06 | 6.2E+06 |
| MUC5B | 17289 | 3.4E+05 | 8.9E+04 | 3.6E+05 | 3.9E+06 |
| DST | 17028 | 1.1E+07 | 2.5E+06 | 3.5E+06 | 7.1E+06 |
| MUC5AC | 16965 | 1.6E+06 | 3.2E+05 | 2.1E+05 | 6.5E+05 |
| HMCN1 | 16908 | 1.9E+05 | 8.7E+05 | 3.6E+05 | 5.7E+05 |

TABLE 2-continued

Expression of long proteins in genomes in 29 organs and tissues of healthy human

| | | | | | |
|---|---|---|---|---|---|
| MDN1 | 16791 | 1.9E+07 | 2.3E+06 | 1.0E+06 | 4.8E+05 |
| KMT2D | 16614 | 2.7E+05 | 2.4E+07 | 4.2E+05 | 6.1E+04 |
| MUC4 | 16239 | 0.0E+00 | 0.0E+00 | 8.0E+05 | 1.0E+06 |
| MUC12 | 16008 | 0.0E+00 | 0.0E+00 | 0.0E+00 | 0.0E+00 |
| RNF213 | 15771 | 4.1E+06 | 7.8E+06 | 3.3E+07 | 3.1E+07 |
| UBR4 | 15552 | 2.0E+07 | 2.1E+07 | 1.5E+07 | 1.6E+07 |
| PCLO | 15429 | 6.0E+04 | 5.7E+05 | 2.4E+05 | 6.4E+05 |
| HYDIN | 15366 | 3.1E+06 | 1.8E+06 | 1.1E+06 | 0.0E+00 |
| EPPK1 | 15267 | 2.2E+06 | 7.3E+05 | 2.6E+07 | 7.4E+07 |
| KIAA1109 | 15018 | 2.6E+05 | 5.5E+05 | 6.1E+05 | 9.3E+05 |

The inventors found for the first time that most of the particularly long proteins had tissue-specific expression. For example, TTN, the longest gene in the human genome, and OBSCN, the third longest gene, were also specifically expressed in myocardium. In addition, MUC16, the second longest gene, and SYNE2, the sixth gene, were both highly expressed in a reproductive system. By analyzing the expression of these long proteins in the human tissues and organs, the inventors pointed out that when the HHT was used for antiviral treatment in human, it was necessary to pay special attention to the expression changes of these long proteins, and evaluate the damage.

(6) Effect of HHT for treating SARS-CoV-2 infection in Vero-E6 cell

1. Tested drugs: see Table 3 for drug names and concentrations.

2. Cells: VeroE6 cells, stored in the Viral Laboratory of State Key Laboratory of Respiratory Disease, Guangzhou Institute of Respiratory Health.

3. Virus: SARS-CoV-2, with a titer of $TCID_{50}=10^6/100$ μL, stored at −80° C. by BSL-3 Laboratory of Guangzhou Customs Technology Center (Laboratory of Highly Pathogenic Microbes, State Key Laboratory of Respiratory Disease). The virus titer used was 100 $TCID_{50}$.

(1) Tested drug:

TABLE 3

Drug names, experimental concentrations and grouping

| Grouping | | Drug concentration (μM) |
|---|---|---|
| Experimental group 1 | HHT | 1.5, 0.75, 0.375 and 0.186 |
| Virus control group | SARS-COV-2 virus solution | 100 $TCID_{50}$/well |
| Cell control group | Medium | |

(2) 100 μL of Veroe6 cells with a concentration of $2\times10^5$ cells/mL were added to each well of a sterile 96-well culture plate, and cultured in 5% CO2 at 37° C. for 24 hours.

(3) The 100 $TCID_{50}$ virus solution was added into to the culture plate experimental group and the virus control group with the amount of 100 μL/well, incubated in a 5% CO2 incubator at 37° C. for 2 hours.

(4) After 2 hours, the cell culture fluid in the 96-well culture plate was discarded. The tested drugs were diluted to various concentrations in Table 1, each concentration was added in triplicate wells, and the above-mentioned drugs was added in a concentration of 100 μL/well.

(5) Cell control, blank control (solvent control), virus control (negative control) and positive drug control (chloroquine or remdesivir) were established at the same time.

(6) The cells were incubated in 5% CO2 incubator at 37° C. for 3 days to 4 days.

(7) The cytopathic effect (CPE) was observed under an optical microscope, and the degree of the CPE was recorded according to the following six standard: "−" denoted no CPE; "±" denoted that the CPE was less than 10%; "+" denoted that the CPE was about 25%; "++" denoted that the CPE was about 50%; "+++" denoted that the CPE was about 75%; and "++++" denoted that the CPE was more than 75%. A half effective concentration (IC50) was calculated by Reed-Muench method or GraphPad Prism5.0. Efficacy judging standard: a concentration with 50% inhibition of the virus CPE was regarded as an effective concentration.

(8) Experimental conditions: all the above experimental operations were completed in the BSL-3 Laboratory.

After observing the cytopathic effect (CPE) and recording the experimental results, the half effective concentration (IC50) was calculated by Reed-Muench method or GraphPad Prism5.0. The experimental results were shown in Table 4 below and FIG. 5.

TABLE 4

Efficacy results of HHT against SARS-CoV-2

| Drug concentration (μM) | Inhibition rate (%) |
|---|---|
| 1.50 | 93.33 ± 2.89 |
| 0.75 | 86.67 ± 2.89 |
| 0.375 | 60.00 ± 8.66 |
| 0.186 | 31.67 ± 7.64 |

Figure 5:
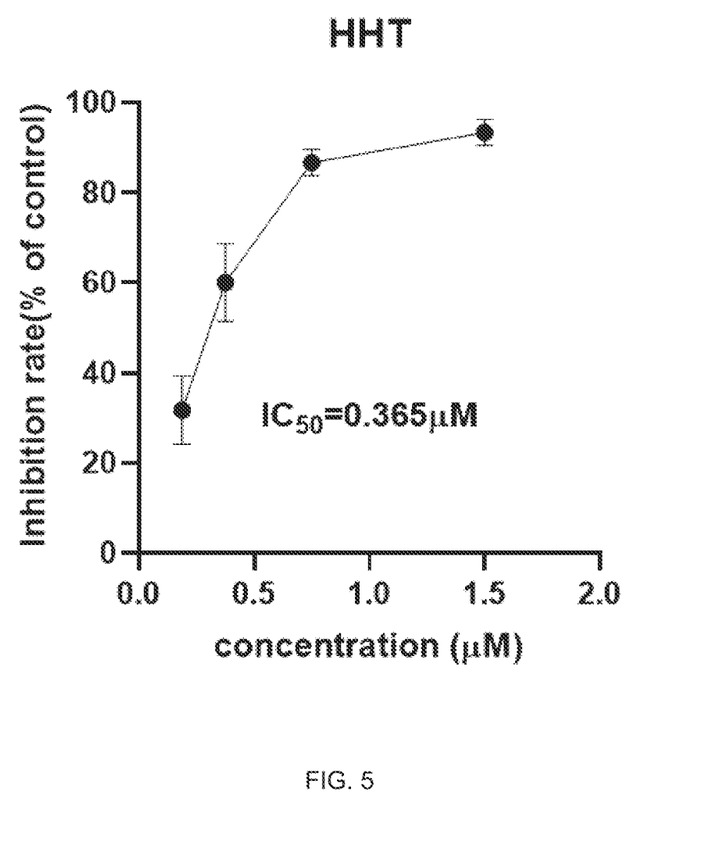

It could be seen from the results in Table 4 and FIG. 5 that the HHT could significantly inhibit the cytopathic effect of the Vero E6 cells infected by the SARS-CoV-2 at a concentration about 1 micromolar, indicating that the HHT could be used as an effective component against SARS-CoV-2 and other Betacoronaviruses.

(7) Effect of HHT for treating SARS-CoV-2 infection in mouse model

1. Tested drug: HHT

2. Animal: male ACE2 humanized mice, provided by Guangzhou Institutes of Biomedicine and Health.

3. Virus: SARS-CoV-2, from Guangdong Provincial Center for Disease Control and Prevention, amplified and cultured by Kunming Institute of State Biological Safety Primate, Kunming Institute of Zoology, Chinese Academy of Sciences, and stored at −80° C. The infection dose was $2\times10^6$ $TCID_{50}$.

Experimental Method:

1. On the day of virus infection, male ACE2 humanized mice were weighed first, and then HHT was injected intraperitoneally (dose: 80 μg/200 μL).

2. After the HHT was injected for 2 hours, the mice were infected by intranasal infection with a virus dose of $2 \times 10^6$ TCID$_{50}$.

3. The ACE2 humanized mice were weighed every day after infection, and the HHT (40 μg/200 μL/day) was injected intraperitoneally on the first and second days after infection.

4. The mice were euthanized and dissected on the third day after infection, lung tissues were taken, viral load of lung tissues is detected, and HE staining is conducted.

5. The method for detecting the viral load in the lung tissues was: extracting tissue RNAs by TRIzol method, then detecting the viral load in the lung tissues by one-step RT-qPCR method (TaqMan method). The results of the viral loads were expressed as copies/μg of the total RNA.

Figure 6A:
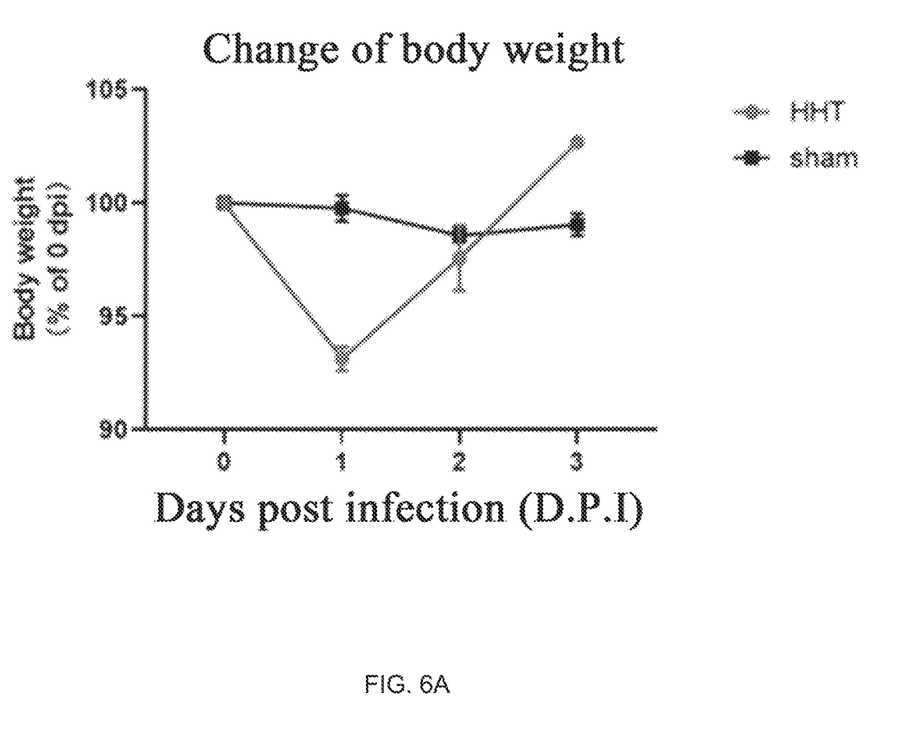
Figure 6B:
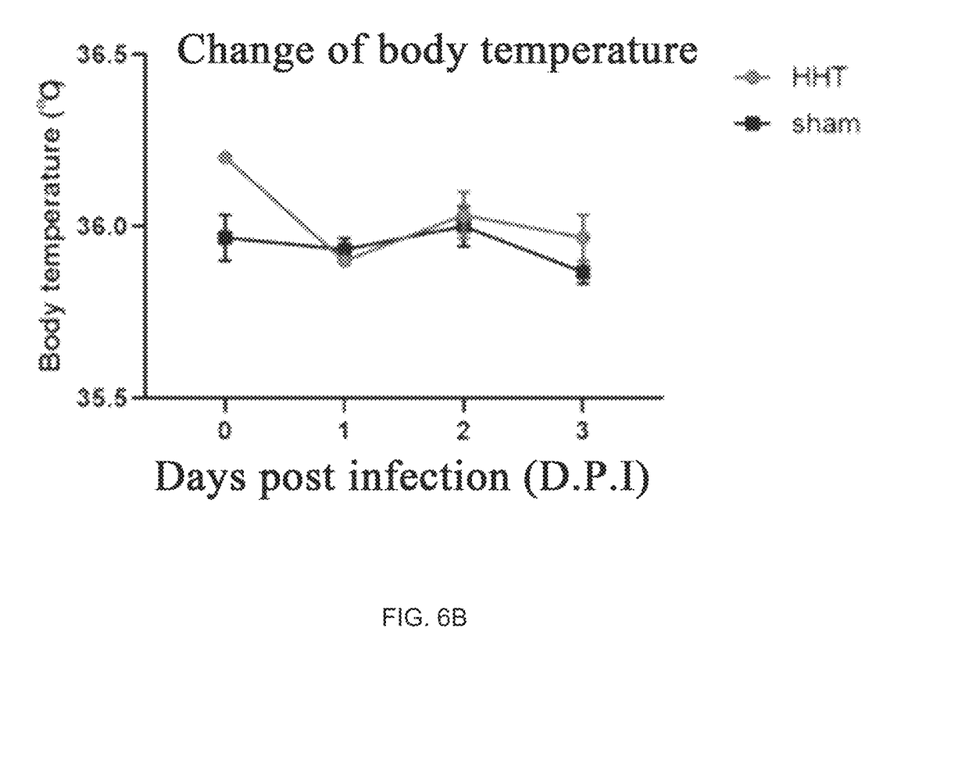
Figure 6C:
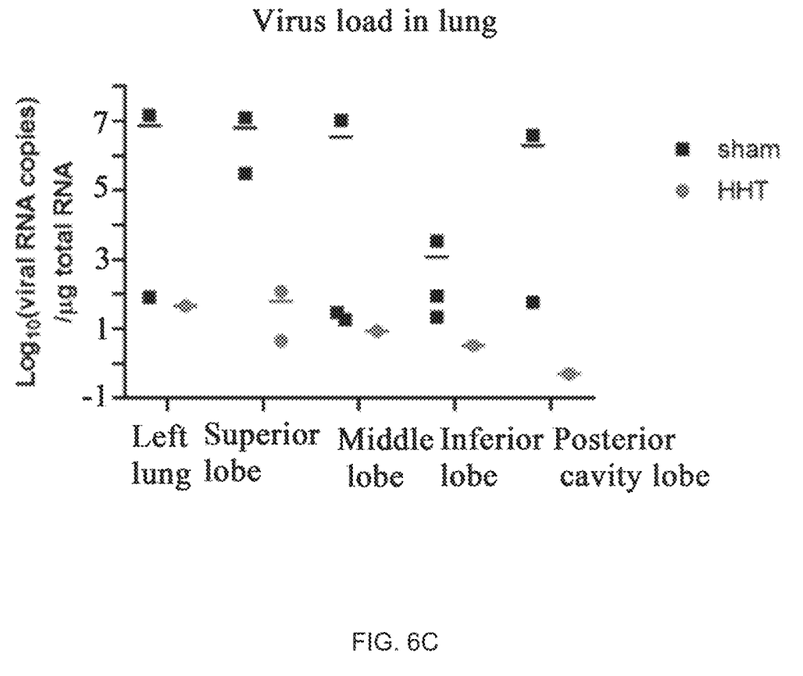

The results were as shown in FIG. 6A, FIG. 6B and FIG. 6C. It could be seen from FIG. 6 A, FIG. 6B and FIG. 6C that the HHT could effectively eliminate the infectedSARS-CoV-2 in the mouse models within a safe dose range, indicating that the HHT could be used as an effective component against SARS-CoV-2 and other betacoronaviruses.

The embodiments of the present disclosure skillfully take the betacoronavirus as the treatment target, and has the following advantages: 1) the first step of the coronavirus replication needs to translate a very long protein (the protein encoded by ORF1ab is nearly 800 KDa); 2) among the coronaviruses, the protein encoded by the ORF1ab of beta-coronavirus is longer than that of the alphacoronavirus and gammacoronavirus; 3) in the host cells (mammalian cells) of the betacoronavirus, protein products of most genes are much shorter than 800 KDa, while half-lives of the gene products (comprising mRNA and protein) encoding long proteins are relatively long, so the betacoronavirus has little effect on the homoharringtonine; and 4) in the host cells of the betacoronavirus, the gene encoding long proteins is specifically expressed in tissues in general, which can further reduce the influence of the homoharringtonine.

The embodiments of the present disclosure provide use of the homoharringtonine in preparation of the drug for treating SARS-CoV-2 infection. It is confirmed for the first time that the homoharringtonine has an inhibitory effect on the SARS-CoV-2, can effectively eliminates the SARS-CoV-2 infection in the Vero-E6 cells, and effectively inhibit the virus from infecting host animals (mice). Therefore, the homoharringtonine can be used as an effective component against the SARS-CoV-2 and other betacoronaviruses.

The above embodiments are some embodiments of the present disclosure, but the embodiments of the present disclosure are not limited to the above embodiments, and any other changes, modifications, substitutions, combinations, and simplifications made without departing from the spirit and scope of the present disclosure should be equivalent replacement means, and are included in the protection scope of the present disclosure.

The invention claimed is:

1. A method for treating a disease caused by a betacoronavirus, consisting of administering a therapeutically effective amount of homoharringtonine to a patient, wherein the betacoronavirus is SARS-CoV-2, and a concentration of homoharringtonine is about 1 micromolar.

2. A method for treating a disease caused by a betacoronavirus, consisting of administering a therapeutically effective amount of a drug against betacoronavirus infection to a patient, wherein the drug consists of a therapeutically effective amount of homoharringtonine, the betacoronavirus is SARS-CoV-2, and a concentration of homoharringtonine is about 1 micromolar.

3. A method for treating a disease caused by a betacoronavirus, consisting of administering a therapeutically effective amount of a betacoronavirus replication inhibitor to a patient, wherein the inhibitor consists of a therapeutically effective amount of homoharringtonine, the betacoronavirus is SARS-CoV-2, and a concentration of homoharringtonine is about 1 micromolar.

4. A method for treating a disease caused by a betacoronavirus, consisting of administering a therapeutically effective amount of a formulation to a patient, wherein the formulation consists of a therapeutically effective amount of homoharringtonine, the betacoronavirus is SARS-CoV-2, and a concentration of homoharringtonine is about 1 micromolar.

5. The method according to claim 2, wherein the drug is in a dosage form of injection, oral formulation or inhalant.

6. The method according to claim 3, wherein the inhibitor is in a dosage form of injection, oral formulation or inhalant.

7. The method according to claim 4, wherein the formulation is in a dosage form of injection, oral formulation or inhalant.

* * * * *